US00RE42867E

(19) United States
(12) Reissued Patent
Hammill, Sr. et al.

(10) Patent Number: US RE42,867 E
(45) Date of Reissued Patent: Oct. 25, 2011

(54) BONE FIXATION SYSTEM WITH LOW PROFILE FASTENER

(75) Inventors: John E. Hammill, Sr., Rossford, OH (US); Robert Doubler, Monroe, MI (US)

(73) Assignee: Spinal, LLC, Toledo, OH (US)

(21) Appl. No.: 11/799,469

(22) Filed: May 9, 2008

Related U.S. Patent Documents

Reissue of:
(64) Patent No.: 7,090,674
Issued: Aug. 15, 2006
Appl. No.: 10/701,349
Filed: Nov. 3, 2003

(51) Int. Cl.
*A61B 17/70* (2006.01)

(52) U.S. Cl. ..... 606/277; 606/309; 606/60

(58) Field of Classification Search ..... 606/264, 606/265, 266, 267, 269, 270, 271, 272, 277, 606/306, 309, 60, 246
See application file for complete search history.

(56) References Cited

U.S. PATENT DOCUMENTS

| | | | | | |
|---|---|---|---|---|---|
| 255,248 | A | * | 3/1882 | Graham | 322/95 |
| 255,428 | A | | 3/1882 | Graham | |
| 486,196 | A | * | 11/1892 | Ridsdale et al. | 508/152 |
| 590,294 | A | * | 9/1897 | Archer | 411/268 |
| 4,378,187 | A | * | 3/1983 | Fullerton | 411/267 |
| 4,419,026 | A | * | 12/1983 | Leto | 403/104 |
| 4,836,196 | A | * | 6/1989 | Park et al. | 606/246 |
| 4,854,304 | A | * | 8/1989 | Zielke | 606/276 |
| 4,887,595 | A | * | 12/1989 | Heinig et al. | 606/254 |
| 4,887,596 | A | * | 12/1989 | Sherman | 606/305 |
| 4,946,458 | A | * | 8/1990 | Harms et al. | 606/305 |
| 4,950,269 | A | | 8/1990 | Gaines, Jr. | |
| 5,002,542 | A | * | 3/1991 | Frigg | 606/264 |
| 5,110,244 | A | * | 5/1992 | Garman | 411/361 |
| 5,129,900 | A | * | 7/1992 | Asher et al. | 606/264 |
| 5,133,717 | A | * | 7/1992 | Chopin | 606/301 |
| 5,324,150 | A | * | 6/1994 | Fullerton | 411/433 |
| 5,427,488 | A | * | 6/1995 | Fullerton et al. | 411/433 |
| 5,443,467 | A | * | 8/1995 | Biedermann et al. | 606/65 |
| 5,487,744 | A | * | 1/1996 | Howland | 606/264 |
| 5,549,608 | A | * | 8/1996 | Errico et al. | 606/264 |

(Continued)

FOREIGN PATENT DOCUMENTS

EP 0 836 835 A3 7/1998

(Continued)

OTHER PUBLICATIONS

Wright Medical Technology, Inc, Versalok Low Back Fixation System—Instrumentation Manual, 1997, 1-10, Wright-Medical Technology, Inc.—Arlington, Tenn.

(Continued)

*Primary Examiner* — Pedro Philogene
(74) *Attorney, Agent, or Firm* — Carter, DeLuca, Farrell & Schmidt, LLP

(57) ABSTRACT

A low profile orthopedic device is used to fix and stabilize bones to correct anomalies in skeletal structure occurring naturally or by trauma. Bone screws are screwed into bones by application of torque. Clamps are movably attached to the screws. Each clamp includes a compression ring. A connecting rod connects several screws through slots in the clamps. The clamps are tightened to hold the rod and the heads in a pre-selected position by linear movement of the compression rings.

73 Claims, 8 Drawing Sheets

U.S. PATENT DOCUMENTS 5,569,247 A * 10/1996 Morrison ..... 606/264
5,584,834 A * 12/1996 Errico et al. ..... 606/264
5,591,166 A * 1/1997 Bernhardt et al. ..... 606/266
5,613,816 A * 3/1997 Cabahug ..... 411/433
5,628,740 A * 5/1997 Mullane ..... 606/307
5,653,765 A * 8/1997 McTighe et al. ..... 623/22.42
5,669,911 A * 9/1997 Errico et al. ..... 606/264
5,683,392 A * 11/1997 Richelsoph et al. ..... 606/272
5,716,357 A * 2/1998 Rogozinski ..... 606/264
5,733,285 A * 3/1998 Errico et al. ..... 606/278
5,749,690 A * 5/1998 Kutz ..... 411/431
5,788,443 A * 8/1998 Cabahug ..... 411/385
5,800,108 A * 9/1998 Cabahug ..... 411/433
5,800,435 A * 9/1998 Errico et al. ..... 606/261
5,863,293 A * 1/1999 Richelsoph ..... 606/278
5,964,760 A * 10/1999 Richelsoph ..... 606/279
5,997,539 A * 12/1999 Errico et al. ..... 606/278
6,010,503 A * 1/2000 Richelsoph et al. ..... 606/278
6,050,997 A * 4/2000 Mullane ..... 606/250
6,063,090 A * 5/2000 Schlapfer ..... 606/270
6,090,111 A * 7/2000 Nichols ..... 606/266
6,102,952 A * 8/2000 Koshino ..... 623/20.21
6,132,432 A * 10/2000 Richelsoph ..... 606/278
6,162,234 A * 12/2000 Freedland et al. ..... 606/151
6,187,005 B1 * 2/2001 Brace et al. ..... 606/264
RE37,227 E * 6/2001 Brodbeck ..... 433/173
6,254,602 B1 * 7/2001 Justis ..... 606/272
6,273,888 B1 * 8/2001 Justis ..... 606/272
6,355,040 B1 * 3/2002 Richelsoph et al. ..... 606/272
RE37,665 E * 4/2002 Ralph et al. ..... 606/278
6,416,515 B1 * 7/2002 Wagner ..... 606/250
6,454,773 B1 * 9/2002 Sherman et al. ..... 606/78
6,478,798 B1 * 11/2002 Howland ..... 606/264
6,565,565 B1 * 5/2003 Yuan et al. ..... 606/272
6,595,992 B1 * 7/2003 Wagner et al. ..... 606/250
6,602,255 B1 * 8/2003 Campbell et al. ..... 606/290
6,610,062 B2 * 8/2003 Bailey et al. ..... 606/261
6,610,063 B2 * 8/2003 Kumar et al. ..... 606/250
6,623,485 B2 * 9/2003 Doubler et al. ..... 606/301
6,626,906 B1 * 9/2003 Young ..... 606/278
7,105,029 B2 9/2006 Doubler et al.
7,335,201 B2 2/2008 Doubler et al.
7,658,582 B2 2/2010 Doubler et al.
2002/0114680 A1 * 8/2002 Stoewer et al. ..... 411/361
2003/0149487 A1 * 8/2003 Doubler et al. ..... 623/23.44
2005/0053423 A1 3/2005 Doubler et al.
2007/0286703 A1 12/2007 Doubler et al.

FOREIGN PATENT DOCUMENTS

EP 0836835 * 7/1998
EP 0 947 174 A3 5/2001
EP 0947174 * 5/2001

OTHER PUBLICATIONS

Osteotech Inc. Spinal Systems, Versalok Low Back Fixation System—Instrumentation Manual, 1999, 1-11, Osteotech, Inc. Spinal Systems.—Eatontown, New Jersey.

* cited by examiner

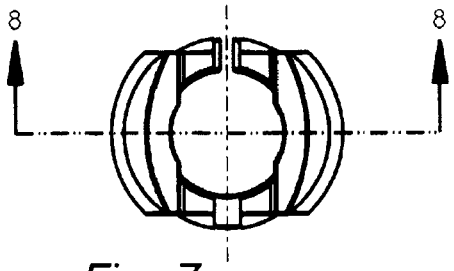
Fig. 7
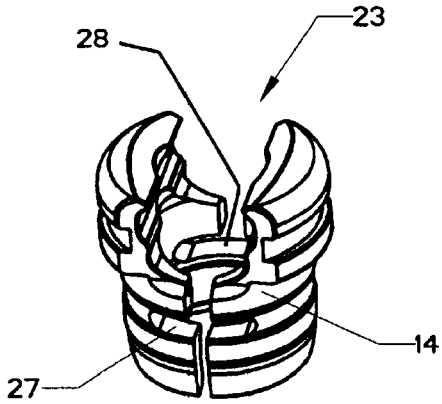
Fig. 9
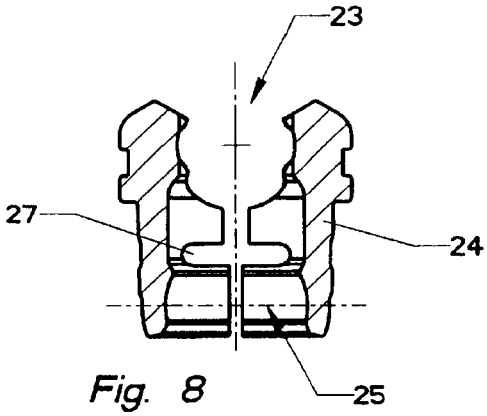
Fig. 8
Fig. 11
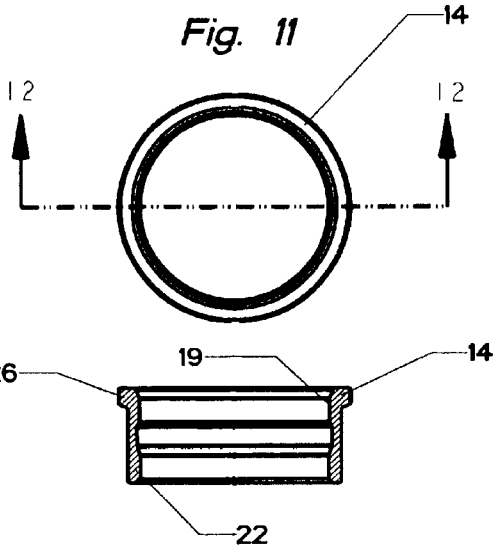
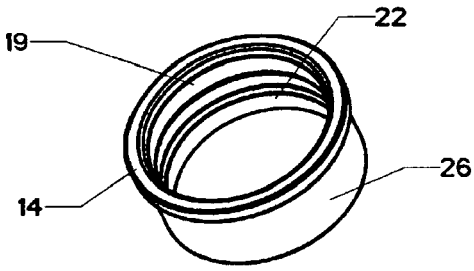
Fig. 10
Fig. 12

Fig. 13
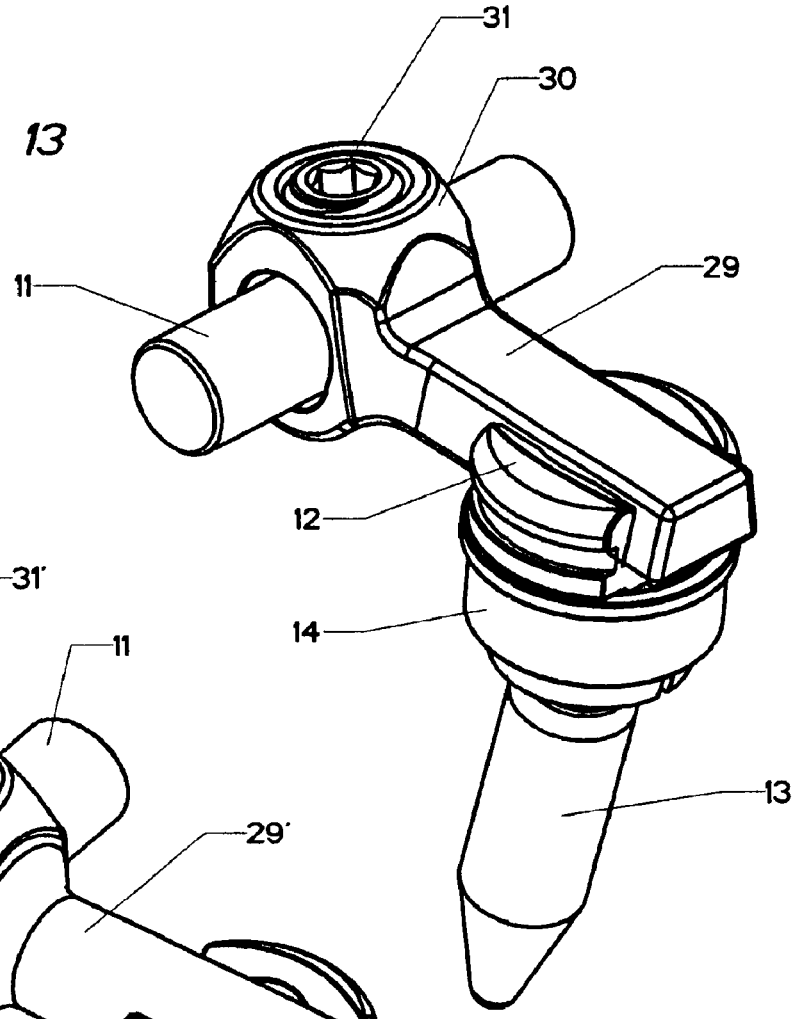
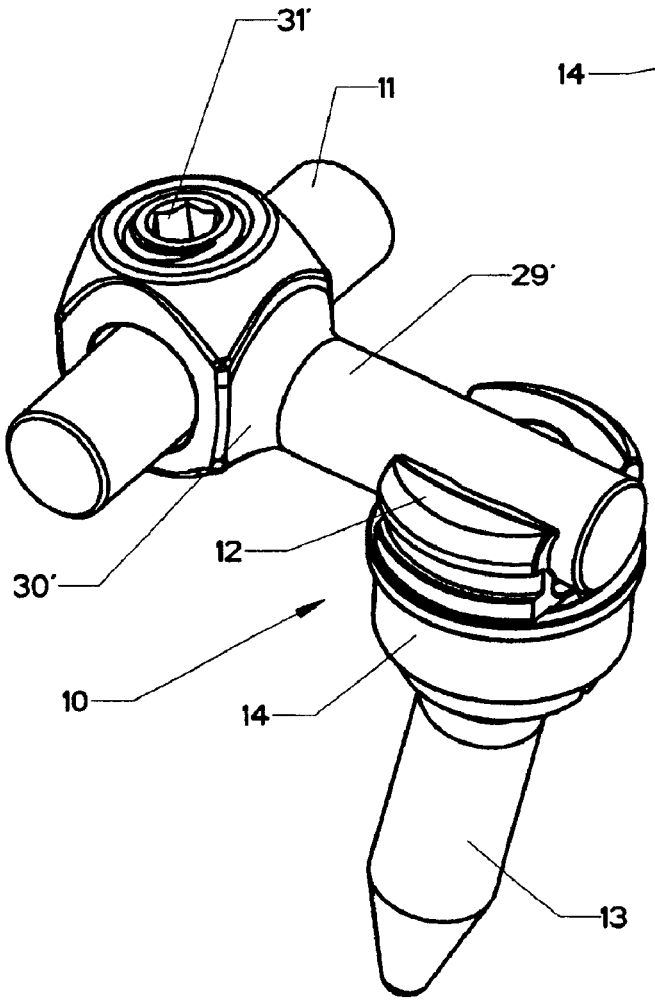
Fig. 14

Fig. 18
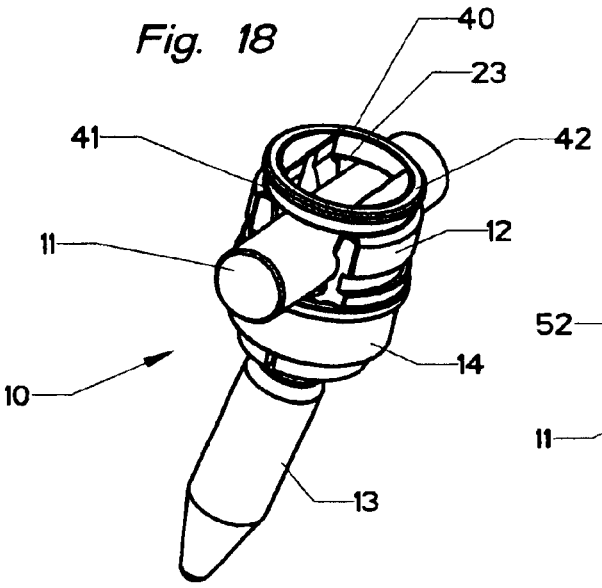
Fig. 20
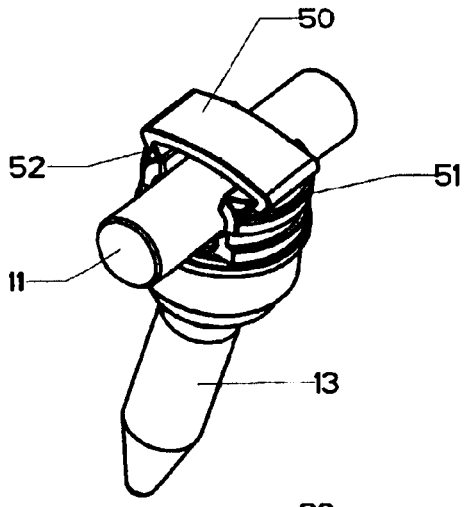
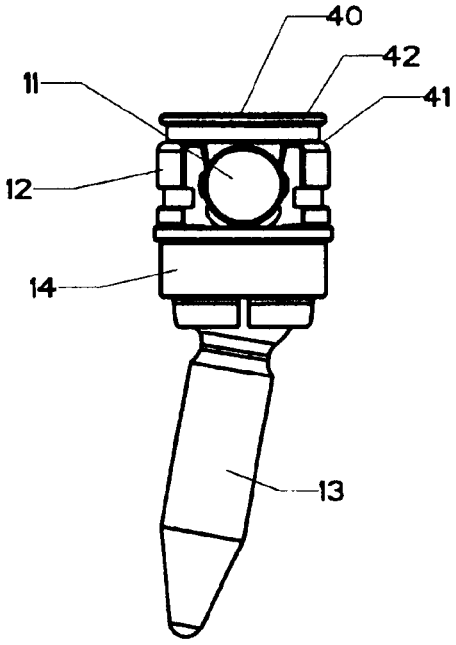
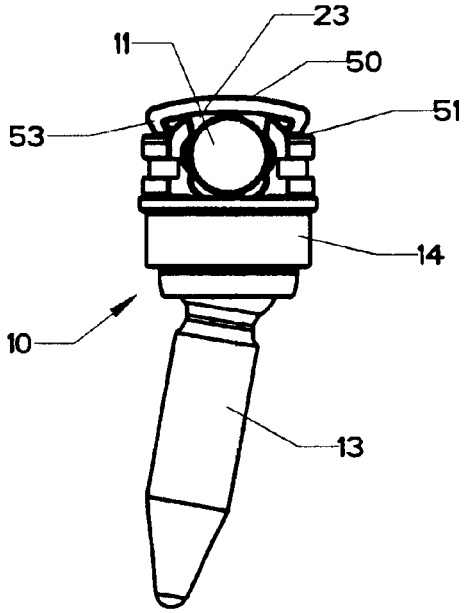
Fig. 19
Fig. 21

BONE FIXATION SYSTEM WITH LOW PROFILE FASTENER

Matter enclosed in heavy brackets [ ] appears in the original patent but forms no part of this reissue specification; matter printed in italics indicates the additions made by reissue.

BACKGROUND OF THE INVENTION

1. Field of the Invention

This invention relates to orthopedic surgery and, in particular, to devices and prosthesis for stabilizing and fixing bones and joints of the body.

2. Description of the Prior Art

Published U.S. Application, US 2003/0149487 A1, published Aug. 7, 2003, teaches the use of a linear movement to apply compressive forces to connect components of an artificial hip joint.

U.S. Pat. No. 6,626,906 issued Sep. 30, 2003 to Young teaches a spinal rod attached to a spinal anchor by a clamp. The clamp is tightened about the anchor by a collet screwed into the clamp. The rod is held in the clamp by a split ring that is reduced in size by the collet. The anchor is placed in the bone by torque and the collet is tightened by additional torque.

U.S. Pat. No. 6,610,063 issued Aug. 26, 2003 to Kumar et al, U.S. Pat. No. 6,610,062 issued Aug. 26, 2003 to Bailey et al, U.S. Pat. No. 6,565,565 issued May 20, 2003 to Yuan et al, U.S. Pat. No. RE 37,665 issued Apr. 16, 2002 to Ralph et al, U.S. Pat. No. 6,478,798 issued Nov. 12, 2002 to Howland and U.S. Pat. No. 5,584,834 issued Dec. 17, 1996 to Errico et al teach a spinal rod coupled to several bone anchors by clamps that require additional torque to be applied to the assembly after the bone screw has been seated in the bone.

In normal practice, the bone screws are each anchored in the bone with a specific amount of torque that approaches the ultimate sustainable force between the screw threads and the bone. The bone screws are then connected together by a rod having sufficient stiffness to maintain the desired skeletal orientation. The connection between the rod and the bone screws must be strong enough to be immobile.

All these prior art spinal fixation devices result in additional torque applied to the assembly, and thereby to the bone screw, to tighten and lock the rod to each of the bone screws. The additional load may strip the purchase between the bone and the threads of the bone screw. To prevent such a result, some tool must be used to counter the torque of locking the rod and the screws. The use of an anti-torqueing tool requires additional coordination by the surgeon or surgeons to prevent slippage.

What is needed in the art is a system for connecting a rod and an embedded bone screw using compressive forces rather than torque.

SUMMARY OF THE PRESENT INVENTION

There are many instances in which it is necessary to stabilize and fix bones and bone fragments in a particular spatial relationship to correct the location of skeletal components due to injury or disease. One group of devices employ a number of bone pins, anchors, or screws placed in bones across a discontinuity in the bone or bone fragments, such as a fracture, or adjacent vertebrae, or a joint, connected by a rod to maintain a predetermined spatial location of the bones. In some cases these devices may be temporary, with subsequent removal, or permanent, in the form of a prosthesis. The devices may be internal or external of the body. The instant device may be used in these applications. However, the preferred embodiment is related to spinal fixation and the description is directed thereto by way of example and not limitation.

SHORT DESCRIPTION OF THE DRAWINGS

FIG. 7 is a top plan view of the clamp body of this invention;

FIG. 8 is a side view, partially in section, of the clamp body of this invention;

FIG. 9 is a perspective of the clamp body of this invention;

FIG. 10 is a perspective of the compression ring of this [invnetion] *invention*;

FIG. 11 is a top view of the compression ring of this invention;

FIG. 12 is a cross section of the compression ring of this invention;

FIG. 13 is a perspective of another embodiment of this invention;

FIG. 14 is a perspective of another embodiment of this invention;

FIG. 18 is a perspective of another embodiment of this invention with the compression ring in the open position;

FIG. 19 is a side view of FIG. 18 with the compression ring in the closed position;

FIG. 20 is a perspective of another embodiment of this invention with the compression ring in the open position;

FIG. 21 is a side view of FIG. 20 with the compression ring in the closed position;

DETAILED DESCRIPTION OF THE INVENTION

Figure 1:
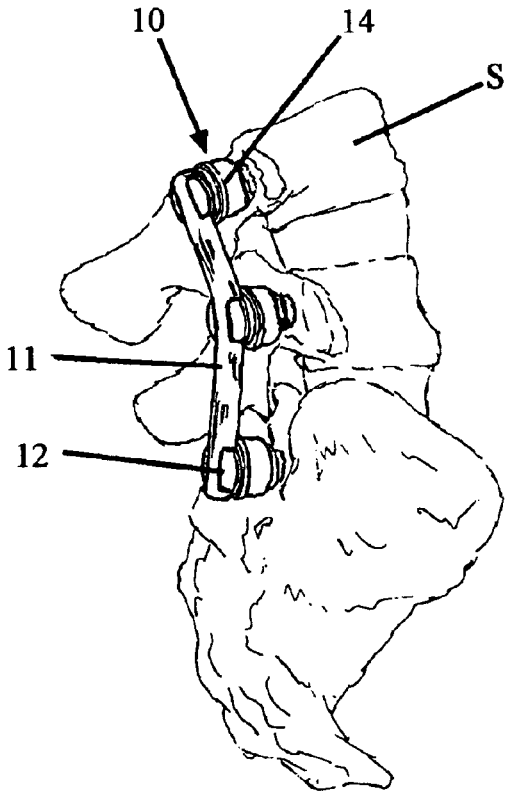
FIG. 1 is a perspective of a portion of the spine with the orthopedic device of this invention in place.
Figure 2:
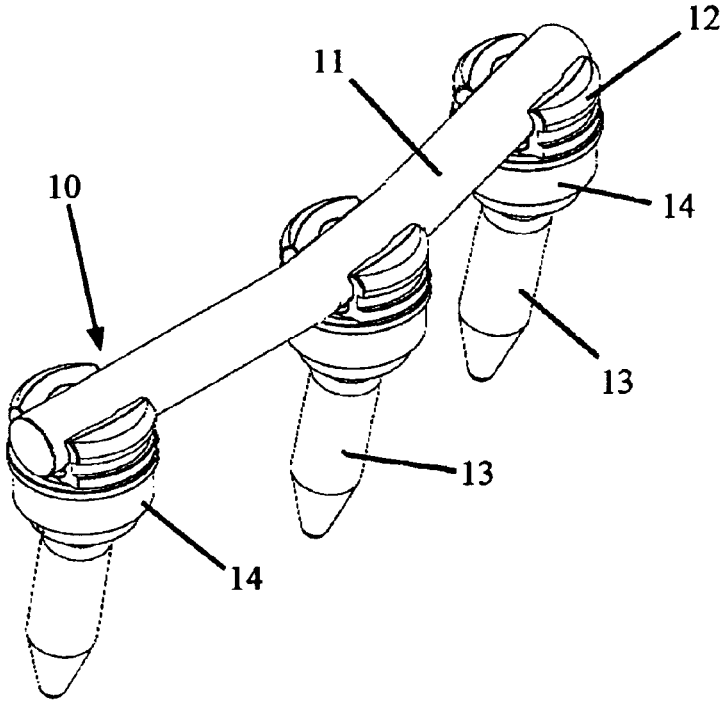
FIG. 2 is a perspective of one embodiment of the orthopedic device of this invention.
Figure 3:
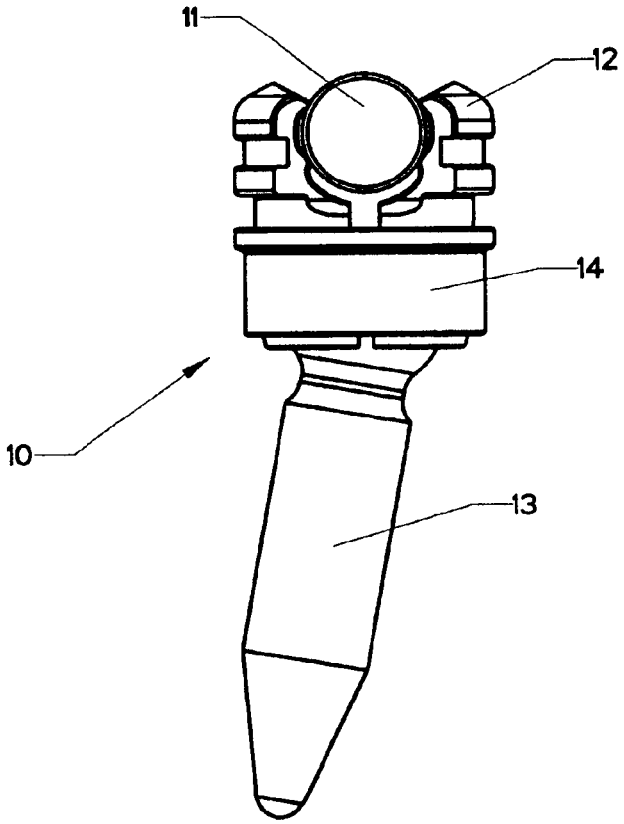
FIG. 3 is an end view, partially in section, of the orthopedic device of this invention with the compression ring in the open position.
Figure 4:
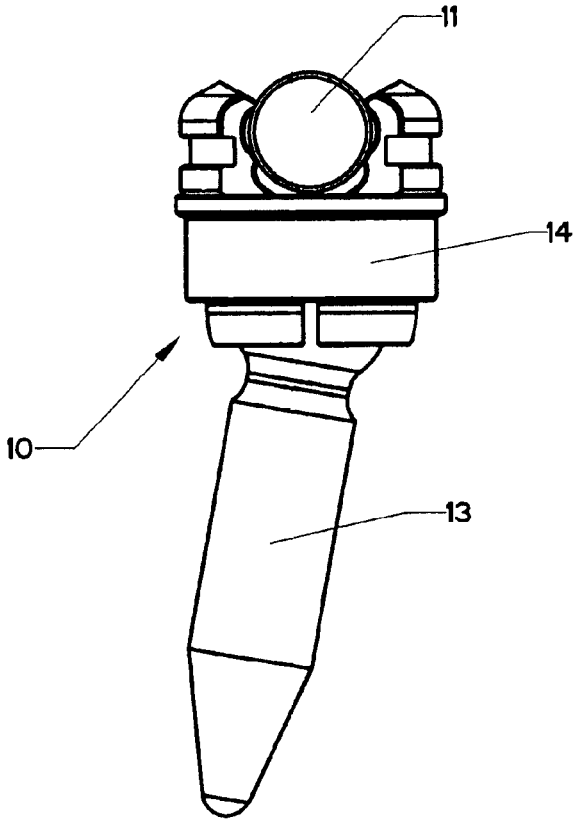
FIG. 4 is an end view, partially in section, of the orthopedic device of this invention with the compression ring in the closed position.

FIG. 1 illustrates a portion of the lumbar spine S with a unilateral orthopedic fixation device 10 in place to stabilize and fix the vertebra in relation to each other and the sacrum in order to maintain a more natural curvature. A bilateral installation can be used, if deemed necessary. As shown in more detail in FIG. 2, an elongated connector bar 11 spans the discontinuity between the vertebra and bone screws 13. As shown, the bar has a circular cross section however, other shapes may be used, such as shown for the link 29 in FIG. 13. The bone anchors have an exterior helical thread 60, shown in FIGS. 5-6, by which the bone screws 13 gain purchase in the cancellous bone through application of torque.

Figure 5:
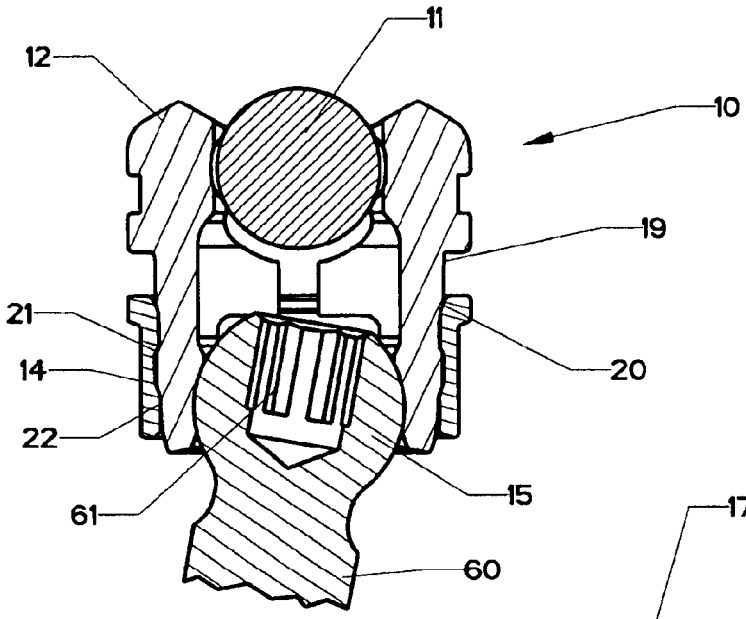
FIG. 5 is a cross section of FIG. 3.
Figure 6:
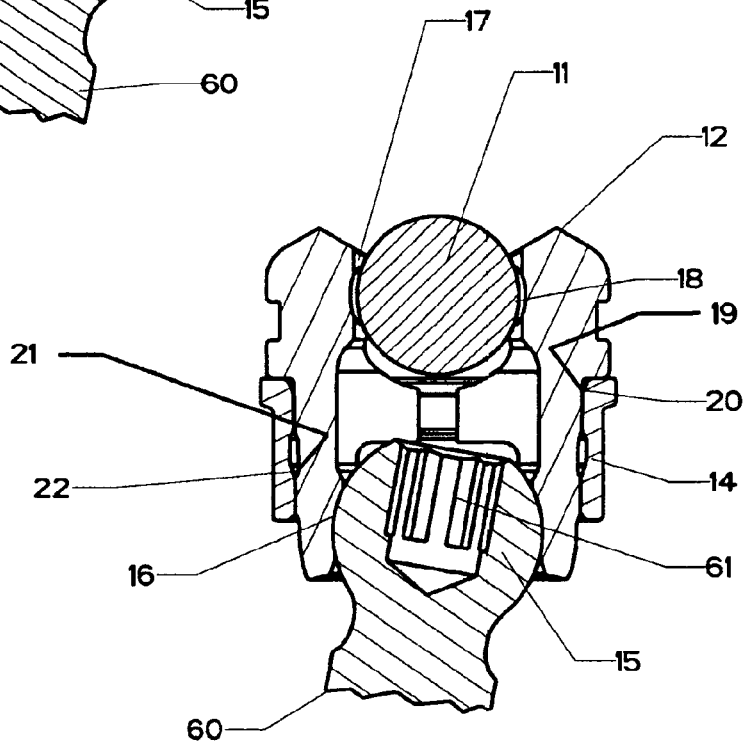
FIG. 6 is a cross section of FIG. 4.

The torque is applied to the screws by the surgeon using a tool (not shown) that engages the recess 61 in the head 15 of the screw and rotates the screw about its longitudinal axis. The amount of torque is critical to installation and the long life of the prosthesis in that too little does not secure the screw from loosening or backing out and too much causes the stripping of the thread path in the bone and loss of purchase. The surgeon attempts to apply the optimum torque when placing the screws in the bone and additional torque on the bone screw is to be avoided. As shown in FIGS. 5 and 6, the recess 61 is accessible through the clamp body 12 which permits pre-assembly of the screw and clamp, if desired, before placement in the bone.

During the spinal fixation, the several bone screws are threaded into the different vertebrae according to the anatomy of each vertebrae. This results in a series of screws without uniformity in angle or alignment. To compensate for these anomalies, the connection between the head of the screws and the clamp bodies pivots or swivels to capture the connector rod. In some instances, the rod must be bent because the screws are so far out of line or the intended correction is so severe. In other cases, a link may be used to secure the rod relative to the bone screw. To avoid application of any more torque to the bone screw, the connector rod 11 is secured to the bone screw by a linear motion which applies compressive force through clamp 12 to the rod 11 and the head 15 of the screw.

The exterior walls 24 of the clamp body 12 are illustrated as generally tubular with a receptacle 25, shown in FIG. 8, at one end and a slot 23 at the other end. The receptacle is of a size to accommodate the head 15 of the bone screw. The slot 23 has upper and lower longitudinal ridges 17 and 18, respectively, to grip the connector rod 11. As shown in FIGS. 5 and 6, the head 15 is spherical and the inside surface 16 of the receptacle is complementary to permit a universal or swivel connection. The orthopedic device has a low profile because the connector rod is recessed in the slot 23 of clamp 12.

The exterior walls 24 of clamp 12 may be tapered or otherwise shaped to provide a change in external diameter along the length. The walls 24 also are relieved with circumferential slots 27 and 28, shown in FIGS. 8-9, to increase the radial flexibility of the clamp. A compression ring 14 is force fit on the exterior walls 24 of the clamp 12 by flexing the tubular walls. The compression ring 14 is moveable along the exterior walls from an open position to a closed position. The open position, as shown in FIGS. 5, 18, and 20, allows swiveling movement of the screw head and sliding movement of the connector rod within the clamp 12. In the closed position, shown in FIGS. 6, 19 and 21, the compression ring 14 applies compressive forces between the clamp 12 and the rod 11 and screw 13 that immobilizes the connections. The compression ring [12] *14* has a skirt 26 with spaced inner annular ridges 19 and 22 which engage annular bulges [19] *20* and 21, respectively, on the exterior walls 24 of clamp 12 in the closed position.

The application of the compressive force that immobilizes the components of the orthopedic device is generated by a linear movement of the compression ring relative to the exterior walls of the clamp. This movement to the closed position is accomplished using a simple telescoping instrument (not shown) engaging the clamp and the compression ring so that equal and opposite forces moves the ring without imparting stress to the screw. In the event of remedial surgery, the clamp may be moved to the open position in the same manner.

The link 29, shown in FIG. 13, extends the range of the orthopedic device in situations where the connector rod cannot directly contact the slot 23 in the clamp 12. The link may come in different lengths or be customized to the size necessary for a particular patient. The link 29 has an arm similar to the dimensions of a connector rod but of a trapezoidal shape though other shapes may be used. The arm has a journal 30 on one end. The journal 30 is shown as a closed ring however, it may be discontinuous. The journal has a threaded bore with a set screw 31 to secure the link to the connector rod. The other end of the link is secured to the bone screw by the clamp 12 and compression ring 14. In FIG. 14, the link 29' arm is the same or similar in shape to a connector rod. The link has a journal 30' with a set screw 31' to fix the connection with the connector rod 11.

Figure 15:
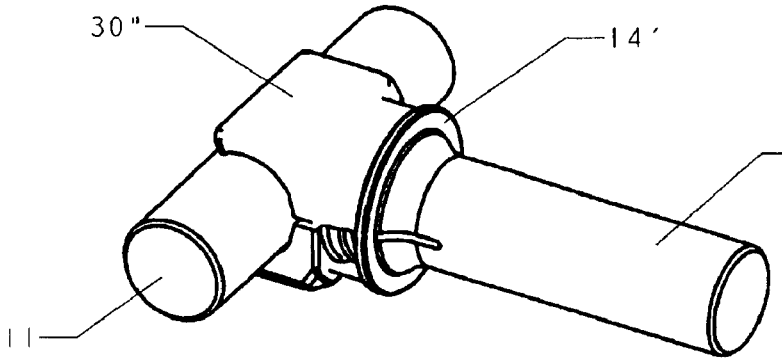
FIG. 15 is a perspective of another embodiment of this invention.
Figure 16:
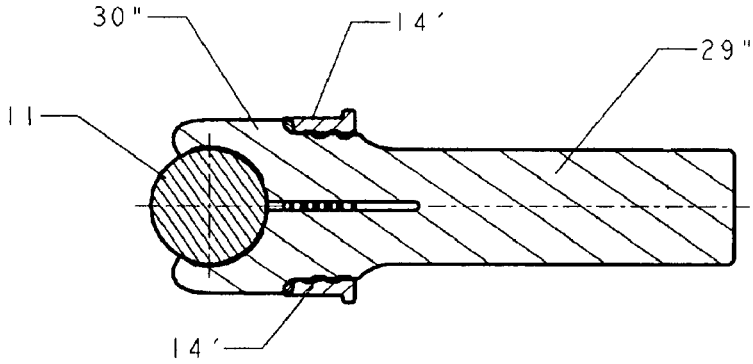
FIG. 16 is a cross section of FIG. 15 showing the compression ring in the open position.
Figure 17:
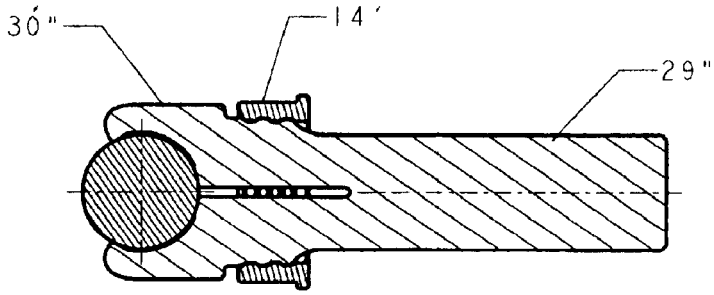
FIG. 17 is a cross section of FIG. 15 showing the compression ring in the closed position.

In FIGS. 15, 16, and 17 another link 29" is illustrated with a journal 30" at one end. The link is similar to a connector rod. The journal 30" is a split sleeve with a compression ring 14' encircling the split sleeve. The compression ring 14' has an open position, shown in FIG. 17, and a closed position, shown in FIG. 16. After adjusting the connection between the link and the connector rod 11, the compression ring is moved to the closed position to secure the link to the connector rod. The other end of the link 29" is secured in the slot of the clamp 12 to complete the tightening of the orthopedic device.

FIGS. 18-23 illustrate embodiments of the orthopedic device 10 in which the clamp 12 includes a retainer preventing the inadvertent separation of the connector rod 11 from the clamp. The use of these clamps and retainers is discretionary with the surgeon. In FIGS. 18 and 19, the exterior walls of the clamp 12 extend above the slot 23 as opposing semi-circular projections. An exterior groove 41 is formed in the semi-circular projections resulting in a terminal lip 42. A retainer ring 40 is snapped into and held in place by the groove 41.

FIGS. 20 and 21 illustrate another retainer in the form of a clip 50 which extends across and covers the open slot 23. The ends 53 of the clip are reverse folded to snap over the lip 52 and seat into the groove 51.

Figure 22:
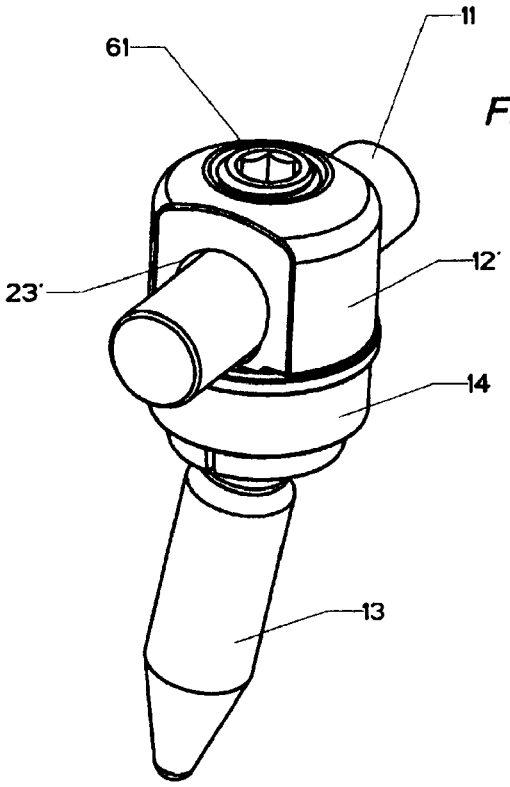
FIG. 22 is a perspective of another embodiment of this invention.
Figure 23:
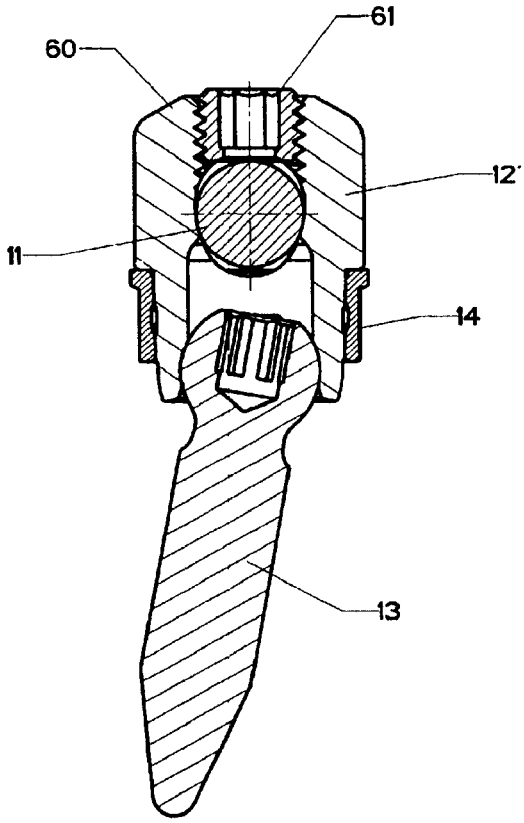
FIG. 23 is a cross section of FIG. 22.

FIGS. 22 and 23 illustrate a clamp 12' with a bore 23' for passage of the connector rod 11. The bore 23' is intersected by a threaded passage 60 with a set screw retainer 61 for holding the connector rod 11 and the clamp 12' together. After the rod 11 is passed through the clamps of an orthopedic device, the compression rings would be moved to the closed position locking the orientation of the rods and screws. The set screws would then be tightened to fix the rod to the clamp. In this way, the torque of tightening the set screw would be absorbed by the rod. The clamp 12' is locked to the screw 13 by compression ring 14, shown in the closed position.

A number of embodiments of the present invention have been described. Nevertheless, it will be understood that various modifications may be made without departing from the spirit and scope of the invention. Accordingly, it is to be understood that the invention is not to be limited by the specific illustrated embodiment but only by the scope of the appended claims.

We claim:

1. An orthopedic device for stabilizing bones including at least one bone pin, at least one elongated connector rod and at least one link interconnecting the elongated connector rod and bone pin, each bone pin comprising a shank for penetrating a bone with a head on one end, a clamp universally connected to said head for locking said pin to a link, said clamp having a body including exterior walls forming an inner receptacle enclosing said head, a first compression ring surrounding the outside of said exterior walls in one position, a slot through said exterior walls of said body opposite said receptacle, said slot slidably contacting said link, said first compression ring linearly movable along said outside of said exterior walls to a second position by application of a force consisting of a linear force along a longitudinal axis of said body whereby said exterior walls of said receptacle and said slot exert compressive force securely locking said clamp about said head and said link, said link having an arm with one end and a journal at the other end, said journal has a split sleeve and a second compression ring surrounding the outside of said split sleeve, said second compression ring being movable linearly along said split sleeve by application of a force consisting of a linear force along an axis of said link to move said sleeve from an open position to a closed position, said open position permitting adjustment of said connector rod in said journal and said closed position securing said connector rod and journal together.

2. An orthopedic device of claim 1 wherein said head of said bone pin is approximately spherical and said receptacle has a complementary shape whereby said bone pin and said clamp may be universally oriented.

3. An orthopedic device of claim 1 wherein said shank is formed with an exterior helical thread.

4. An orthopedic device of claim 1 wherein said slot is adjacent said receptacle whereby said head and said link are in close proximity producing a low profile.

5. In an orthopedic system for stabilizing and fixing bones across a discontinuity, at least two bone screws, an elongated connector rod of a length to span the discontinuity, and at least one link, each said bone screw comprising a threaded shank with a head, said head including a means for applying torque to said shank and a means for attaching one end of said link, the other end of said link formed as a clamp, said clamp having an elongated body with exterior walls, a slot extending across said exterior walls of said clamp, said connector rod movably disposed in said slot, a compression ring surrounding said exterior walls in one position linearly along said exterior walls to a second position by application of a force consisting of a linear force along a longitudinal axis of said link whereby said exterior walls exert a compressive force in said slot when said compression ring is moved by said linear force to said second position.

6. In an orthopedic system of claim 5 wherein said connector rod is slidably engaged in said slot when said compression ring is in said one position, said connector rod is held in said slot when said compression ring is in said second position.

*7. In an orthopedic device for stabilizing bones comprising in combination a bone pin having a first end and a second end, said first end constructed and arranged as a shank portion for securement to a bone, said second end constructed and arranged as a head portion, a clamp universally connected to said head portion of said bone pin, said clamp having an elongated body with exterior walls, a slot extending across said exterior walls, said slot constructed and arranged to accept a rod member, a compression ring surrounding said exterior walls, said compression ring linearly traversable along said exterior walls between a first position and a second position by a force consisting of a linear force, whereby traversal of said compression ring from said first position to said second position compresses said clamp to substantially fix said clamp and said rod to said bone pin in a predetermined orientation, the improvement comprising:*

*at least one annular bulge positioned along the length of said exterior walls of said clamp to provide a change in the external diameter along the length thereof, said at least one annular bulge constructed and arranged to cooperate with said compression ring to apply compressive forces to said clamp for immobilizing at least one of the connections between said clamp and said rod or said clamp and said bone pin.*

*8. The orthopedic device for stabilizing bones of claim 7 wherein said compression ring includes at least one inner annular ridge constructed and arranged to engage said at least one annular bulge in an overlapping manner while said compression ring is in said second position, whereby engagement of said bulge and said ridge applies compressive forces to said clamp for immobilizing the connections between said clamp and said rod with respect to said bone pin.*

*9. The orthopedic device for stabilizing bones of claim 7 wherein the at least one annular bulge is constructed and arranged to cooperate with said compression ring to apply compressive forces to said clamp for immobilizing the connections between said clamp and said rod, the at least one annular bulge constructed and arranged to cooperate with said compression ring to apply compressive forces to said clamp for immobilizing the connections between said clamp and said bone pin, said compression ring constructed and arranged to progressively engage said annular bulge, whereby said connections may be immobilized one at a time.*

*10. The orthopedic device for stabilizing bones of claim 9 wherein said compression ring includes at least one inner annular ridge constructed and arranged to engage the at least one annular bulge in an overlapping manner while said compression ring is in said second position.*

*11. The orthopedic device for stabilizing bones of claim 7, wherein the first position is defined when the compression ring is adjacent the head portion of the bone pin.*

*12. The orthopedic device for stabilizing bones of claim 7 wherein said bone pin is a bone screw wherein said first end includes at least one helical thread for penetrating and engaging a bone and wherein said head portion is substantially spherical in shape.*

*13. An orthopedic device for stabilizing bones comprising:*

*a bone pin having a first end and a second end, said first end constructed and arranged as a shank portion for penetrating securement to a bone, said second end constructed and arranged as a head portion;*

*a clamp universally connected to said head portion of said bone pin for securing said bone pin to a rod or link member, said clamp having an elongated body with exterior walls, said exterior walls including at least one annular bulge to provide a change in the external diameter of said exterior walls, a slot extending across said exterior walls, said slot constructed and arranged to accept said rod or said link member;*

*a compression ring surrounding said exterior walls, said compression ring linearly traversable along said exterior walls between a first position and a second position by application of a force consisting of a linear force along a longitudinal axis of said clamp, whereby traversal of said compression ring from said first position to said second position causes said compression ring to cooperate with said at least one annular bulge to apply compressive forces to said clamp to immobilize at least one of the connections between said clamp and said rod or link member or said clamp and said bone pin.*

*14. The orthopedic device for stabilizing bones of claim 13 wherein said compression ring includes at least one inner annular ridge constructed and arranged to engage said at least one annular bulge in an overlapping manner while said compression ring is in said second position, whereby engagement of said at least one bulge and said at least one ridge applies compressive forces to said clamp for immobilizing at least one of said connections.*

*15. The orthopedic device for stabilizing bones of claim 13 wherein said at least one annular bulge is constructed and arranged to cooperate with said compression ring to apply compressive forces to said clamp for immobilizing at least one of said connections.*

*16. The orthopedic device for stabilizing bones of claim 15 wherein the at least one annular bulge is constructed and arranged to cooperate with said compression ring while said compression ring is in said second position to immobilize the connection between said clamp and said bone pin said second bulge constructed and arranged to cooperate with said compression ring to immobilize the connection between said clamp and said rod or link member while said compression ring is in said second position, whereby said compression ring may independently engage said first or said second bulges during translation thereof.*

*17. The orthopedic device for stabilizing bones of claim 15 wherein said compression ring includes at least one inner annular ridge constructed and arranged to engage the at least one annular bulge in an overlapping manner while said compression ring is in said second position, whereby engagement of said annular bulge and said annular ridge applies compressive forces to said clamp for immobilizing said connections.*

*18. The orthopedic device for stabilizing bones of claim 17 wherein the first position is defined when the compression ring is adjacent the head portion of the bone pin.*

*19. The orthopedic device for stabilizing bones of claim 13 wherein said bone pin is a bone screw wherein said first end includes at least one helical thread for penetrating and engaging a bone and wherein said head portion is at least partially spherical in shape.*

*20. An orthopedic kit for stabilizing bones comprising:*

*at least one bone pin having a first end and a second end, said first end constructed and arranged as a shank portion for penetrating securement to a bone, said second end constructed and arranged as a head portion;*

*a clamp universally connected to said head portion of each said bone pin for securing said bone pin to a rod or a link, said clamp having an elongated body with exterior walls, a slot extending across said exterior walls, said slot constructed and arranged to slidably accept said rod or said link;*

*a first compression ring surrounding said exterior walls of said clamp, said first compression ring linearly traversable along said exterior walls between a first position and a second position by a force consisting of a linear force along a longitudinal axis of said clamp, said first position permitting adjustment of said rod or link, said second position compressing said clamp to immobilize said rod or link with respect to said bone pin;*

*at least one link having an arm on one end and a journal at the other end, said journal having a split sleeve and a second compression ring surrounding an outer surface of said split sleeve, said second compression ring being movable linearly along said split sleeve by application of a force consisting of a linear force along a longitudinal axis of said link to move said sleeve from an open position to a closed position, said open position permitting adjustment of said connector rod in said journal and said closed position securing said connector rod and said journal together;*

*at least one elongated connector rod constructed and arranged to cooperate with said slot or said journal.*

*21. The orthopedic kit for stabilizing bones of claim 20 wherein said clamp includes at least one annular bulge positioned along the length of said exterior walls thereof to provide a change in the external diameter of said clamp, said at least one annular bulge constructed and arranged to cooperate with said first compression ring to apply compressive forces to said clamp for immobilizing the connections between said clamp and said rod or said link with respect to said bone pin.*

*22. The orthopedic kit for stabilizing bones of claim 21 wherein said exterior walls of said clamp include two or more annular bulges to provide a change in the external diameter along the length of said exterior walls, said two or more annular bulges constructed and arranged to cooperate with said first compression ring to apply compressive forces to said clamp for immobilizing the connections between said clamp and said rod or said link with respect to said bone pin.*

*23. The orthopedic kit for stabilizing bones of claim 22 wherein a first of said two or more annular bulges is positioned at a first end of said clamp and second of said two or more annular bulges is positioned at second end of said clamp, said first bulge constructed and arranged to cooperate with said first compression ring while said first compression ring is in said second position to immobilize the connection between said clamp and said bone pin said second ring constructed and arranged to immobilize the connection between said clamp and said rod or said link while said compression ring is in said second position.*

*24. The orthopedic kit for stabilizing bones of claim 22 wherein said first compression ring includes at least one inner annular ridge constructed and arranged to engage at least one of said two or more annular bulges in an overlapping manner while said first compression ring is in said second position, whereby engagement of said bulge and said ridge applies compressive forces to said clamp for immobilizing the connections between said clamp and said rod or said link with respect to said bone pin.*

*25. The orthopedic kit for stabilizing bones of claim 24 wherein said first compression ring includes two or more inner annular ridges, at least one of said ridges constructed and arranged to fit between said two or more annular bulges of said clamp while said compression ring is in said first position and at least one of said ridges constructed and arranged to engage at least one of said two or more annular bulges in an overlapping manner while said compression ring is in said second position to provide compressive forces to said clamp.*

*26. The orthopedic kit for stabilizing bones of claim 20 wherein said bone pin is a bone screw wherein said first end includes at least one helical thread for penetrating and engaging a bone and wherein said head portion is substantially spherical in shape.*

*27. A method of using an orthopedic device to stabilize bones across a discontinuity comprising the steps of:*

*providing a first bone pin having a first end and a second end, said first end constructed and arranged as a shank portion for penetrating securement to a bone, said second end constructed and arranged as a head portion;*

*connecting a first clamp member to said head portion of said first bone pin for universal movement therebetween, said first clamp member having an elongated body with exterior walls, a first compression ring surrounding said exterior walls, said first compression ring located in a first position, a first slot extending across said exterior walls, said first slot constructed and arranged to accept a rod member;*

*securing said shank portion of said first bone pin to a first bone portion on a first side of said discontinuity;*

*providing a second bone pin having a first end and a second end, said first end constructed and arranged as a shank*

*portion for penetrating securement to a bone, said second end constructed and arranged as a head portion;*

*connecting a second clamp member to said head portion of said second bone pin for universal movement therebetween, said second clamp member having an elongated body with exterior walls, a second compression ring surrounding said exterior walls, said second compression ring located in a first position, a second slot extending across said exterior walls, said second slot constructed and arranged to accept a rod member;*

*securing said shank portion of said second bone pin to a second bone portion on a second side of said discontinuity;*

*placing a rod member in said first and said second slots, whereby said rod member extends across said discontinuity;*

*applying a force consisting of a linear force along the longitudinal centerline of said first clamp member for traversing said first compression ring to a second position along said exterior walls of said first clamp member to compress said first clamp member to substantially fix said first clamp and said rod member in a predetermined orientation with respect to said first bone pin;*

*applying a force consisting of a linear force along the longitudinal centerline of said second clamp member for traversing said second compression ring to a second position along said exterior walls of said second clamp member to compress said second clamp member to substantially fix said second clamp member and said rod member in a predetermined orientation with respect to said first bone pin;*

*whereby said bones are stabilized across said discontinuity.*

*28. The method of using an orthopedic device to stabilize bones across a discontinuity of claim 27 wherein said first and said second bone pins are bone screws wherein said first end of each includes at least one helical thread for penetrating and engaging a bone and wherein said head portion of each is substantially spherical in shape.*

*29. The method of using an orthopedic device to stabilize bones across a discontinuity of claim 27 wherein said exterior walls of said first and said second clamp each include at least one annular bulge to provide a change in the external diameter along the length of said exterior walls, said at least one annular bulge constructed and arranged to cooperate with each said respective compression ring to apply compressive forces to said respective clamp for immobilizing the connections between each said respective clamp and said rod with respect to each said respective bone pin.*

*30. The method of using an orthopedic device to stabilize bones across a discontinuity of claim 29 wherein said first and said second compression ring each include at least one inner annular ridge constructed and arranged to engage said at least one annular bulge of a respective clamp in an overlapping manner while each said respective compression ring is located in said second position, whereby engagement between said respective bulges and said ridges apply compressive forces to said respective clamp for immobilizing the connections between said respective clamp and said rod with respect to said respective bone pin.*

*31. An apparatus comprising:*

*a bone screw having a threaded shaft and a screw head;*

*a clamp body having a receptacle sized to accommodate the head of the bone screw with the threaded shaft extending downwardly out of the receptacle; and*

*a compression ring around exterior walls of the clamp body and movable along the exterior walls from an open position to a closed position, the compression ring including an annular flange at the upper edge thereof, the open position defined when the compression ring is moved towards the receptacle.*

*32. The apparatus of claim 31 wherein the screw head is spherical.*

*33. The apparatus of claim 32 wherein the receptacle is configured to receive the spherical screw head.*

*34. The apparatus of claim 31 wherein the receptacle is slotted.*

*35. The apparatus of claim 31 wherein the clamp body has annular bulges which engage annular ridges on the inside of the compression ring with the compression ring in the closed position.*

*36. The apparatus of claim 31 wherein the connection between the screw and the clamp body is a universal connection and the orientation of the screw relative to the clamp body is adjustable with the compression ring in the open position and the orientation between the screw and the clamp body is fixed with the compression ring in the closed position.*

*37. The apparatus of claim 31 wherein the clamp body further comprises a slot to receive a connector rod.*

*38. The apparatus of claim 37 wherein the slot has upper and lower longitudinal ridges to grip the connector rod.*

*39. The apparatus of claim 37 wherein the position of the rod in the slot is adjustable with the compression ring in the open position and is fixed with compression ring in the closed position.*

*40. An apparatus comprising:*

*a bone screw having a threaded shaft and a screw head;*

*a clamp body having a receptacle sized to accommodate the head of the bone screw with the threaded shaft extending out the bottom of the clamp body, the clamp body having a slot to receive a rod;*

*a compression ring around exterior walls of the clamp body and movable along the exterior walls from an open position in which the position of the screw relative to the clamp body is adjustable to a closed position in which the position of the screw relative to the clamp body is fixed; and*

*a retainer which extends across and covers the slot, the retainer remaining rotationally stationary with respect to the clamp body during relative movement of the clamp body and the compression ring.*

*41. The apparatus of claim 40 wherein the retainer is a ring.*

*42. The apparatus of claim 41 wherein the retainer snaps into a groove on the clamp body.*

*43. The apparatus of claim 41 wherein the retainer is a clip.*

*44. The apparatus of claim 43 wherein the ends of the clip seat into a groove of the clamp body.*

*45. An apparatus comprising:*

*a bone screw having a threaded shaft and a screw body;*

*a clamp body having a lower portion defining a receptacle sized to accommodate the head of the bone screw and an upper portion sized to accommodate a rod, the clamp body defining a first diameter near the receptacle and a second diameter near the upper portion, the first diameter being less than the second diameter;*

*a compression ring around exterior walls of the clamp body and movable along the exterior walls from an open position in which the orientation of the screw is adjustable relative to the clamp body and a closed position in which the orientation of the screw is fixed relative to the clamp body, the open position defined when the compression ring is moved towards the receptacle; and*

*a retainer for holding a connector rod and the clamp body together.*

*46. The apparatus of claim 45 wherein the retainer is a set screw retainer.*

*47. The apparatus of claim 45 wherein the clamp body includes a bore for receiving a rod.*

*48. The apparatus of claim 47 wherein the clamp body includes a threaded passage which intersects the bore.*

*49. The apparatus of claim 48 wherein the threaded passage is configured to receive a set screw retainer.*

*50. The apparatus of claim 48 further including a set screw retainer receivable in the threaded passage for holding a rod disposed in the bore and the clamp together.*

*51. An apparatus comprising:*

*a bone screw having a head at one end thereof;*

*a clamp body having a receptacle for receiving the head of the bone screw, the receptacle being transitionable between a first state and a second state;*

*a retainer engageable with the clamp body to hold a connector rod in a relative position with respect to the clamp body; and*

*a ring member operably associated with the clamp body and repositionable from a first position to a second position, the first position defined when the ring member is adjacent the receptacle wherein:*

*when the ring member is in the first position, the receptacle is in the first state and the bone screw is axially adjustable relative to the receptacle, and*

*when the ring member is in the second position, the receptacle is in the second state and the bone screw is fixed relative to the receptacle.*

*52. The apparatus of claim 51 wherein the clamp body includes a saddle for retaining a connector rod.*

*53. The apparatus of claim 51 wherein the ring member is slidably disposed on an outer surface of the clamp body.*

*54. The apparatus of claim 51 wherein the clamp body includes a slot such that opposing walls of the clamp body are repositionable towards and away from each other.*

*55. The apparatus of claim 54 wherein when the ring member is in the second position, the opposing walls of the clamp body are urged towards each other and frictionally engage the head of the bone screw.*

*56. The apparatus of claim 51 wherein the retainer is a clip.*

*57. The apparatus of claim 51 wherein the retainer is a set screw.*

*58. An apparatus comprising:*

*a bone screw having a head at one end thereof;*

*a clamp body having a receptacle for receiving the head of the bone screw, the receptacle transitionable between a first state and a second state;*

*a retainer engageable with the clamp body;*

*a slot defined between the receptacle and the retainer for receiving a connector rod, the retainer holding the connector rod in the slot; and*

*a ring member operably associated with the clamp body such that when the ring member is in a first position the bone screw is axially adjustable relative to the receptacle, and when the ring member is in a second position the bone screw is fixed relative to the receptacle, the first position defined when the ring member is adjacent the receptacle of the clamp body.*

*59. The apparatus of claim 58, wherein the clamp body includes a saddle, the saddle and the retainer defining the slot.*

*60. The apparatus of claim 58, wherein when the ring member is in the second position, the receptacle frictionally engages the head of the bone screw.*

*61. The apparatus of claim 58, wherein the receptacle includes opposing walls that are repositionable towards and away from each other.*

*62. The apparatus of claim 51, wherein the opposing walls frictionally engage the head of the bone screw when the ring member is in the second position.*

*63. The apparatus of claim 58, wherein the retainer is a clip.*

*64. The apparatus of claim 58, wherein the retainer is a set screw.*

*65. The apparatus of claim 58, wherein the ring member is disposed on an outer surface of the clamp body.*

*66. The apparatus of claim 58, wherein the clamp body includes a slot such that opposing walls of the clamp body are repositionable.*

*67. The apparatus of claim 31, wherein the bone screw is pivotable relative to the clamp body when the compression ring is in the open position.*

*68. The apparatus of claim 31, wherein said compression ring includes at least one annular ridge and the clamp body includes at least annular bulge, the annular ridge and the annular bulge engage in an overlapping manner while said compression ring is in said second position, whereby engagement of the annular bulge and the annular ridge applies compressive forces to said clamp for immobilizing said connections.*

*69. The apparatus of claim 31, wherein the annular flange extends radially outward.*

*70. A method of using an orthopedic device to stabilize bones across a discontinuity, comprising:*

*providing a first bone pin assembly, the first bone pin assembly including a first bone screw having a threaded shaft and a screw head, a first clamp body having a receptacle at one end and a first slot at an opposing end, the receptacle sized to accommodate the head of the first bone screw with the threaded shaft extending downwardly out of the receptacle, and a first compression ring around exterior walls of the first clamp body and movable along the exterior walls between an open position and a closed position, the first compression ring including an annular flange at the upper edge thereof, the open position defined when the first compression ring is adjacent the receptacle such that the first bone screw is pivotable relative to the first clamp body;*

*securing the threaded shaft of the first bone pin assembly to a first bone portion on a first side of the discontinuity;*

*placing a rod member in the first slot, whereby the rod member extends across the discontinuity; and*

*repositioning the first compression ring from its open position to its closed position.*

*71. The method of using an orthopedic device to stabilize bones across a discontinuity of claim 70 wherein the exterior wall of the first clamp body includes at least one annular bulge cooperative with the first compression ring to apply compressive forces to the first clamp body for immobilizing the connection between the first clamp body and the rod with respect to the first bone screw.*

*72. The method of using an orthopedic device to stabilize bones across a discontinuity of claim 70, further comprising a second bone pin assembly, the second bone pin assembly including a second bone screw having a threaded shaft and a screw head, a second clamp body having a receptacle at one end and a second slot at an opposing end, the receptacle sized to accommodate the head of the second bone screw with the threaded shaft extending downwardly out of the receptacle, and a second compression ring around exterior walls of the second clamp body and movable along the exterior walls*

*between an open position and a closed position, the second compression ring including an annular flange at the upper edge thereof, the open position defined when the second compression ring is adjacent the receptacle such that the second bone screw is pivotable relative to the second clamp body.*

*73. The method of using an orthopedic device to stabilize bones across a discontinuity of claim 72, further including:*

*securing the threaded shaft of the second bone pin assembly to a second bone portion on a second side of the discontinuity; and*

*repositioning the second compression ring from its open position to its closed position.*

* * * * *